(12) United States Patent
Florin et al.

(10) Patent No.: US 6,783,984 B2
(45) Date of Patent: Aug. 31, 2004

(54) PROCESS FOR THE CRYO-PRESERVATION OF PLANTS

(75) Inventors: Bruno Florin, St. Cyr-sur-Loire (FR); Vincent Petiard, Tours (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/826,393

(22) Filed: Apr. 3, 2001

(65) Prior Publication Data

US 2001/0041364 A1 Nov. 15, 2001

Related U.S. Application Data

(63) Continuation of application No. PCT/EP99/07168, filed on Sep. 27, 1999.

(30) Foreign Application Priority Data

Oct. 7, 1998 (EP) .............................................. 98118938

(51) Int. Cl.⁷ ................................................ C12N 5/04
(52) U.S. Cl. ..................... 435/430.1; 435/430; 435/420
(58) Field of Search .............................. 435/430.1, 430, 435/420

(56) References Cited

U.S. PATENT DOCUMENTS 5,922,929 A * 7/1999 Zimmerman et al. ....... 800/278
5,943,821 A * 8/1999 Ducos et al. ................. 47/58.1
6,143,563 A * 11/2000 Peterson ................... 435/430.1

OTHER PUBLICATIONS

Pence V.C. Cryopreservation of immature embryos of Theobroma cacao. Plant Cell Report. (1991) 10: 144–147.*
Abdelnour–Esquivel et al., "Cryopreservation of Zygotic Embryos of Coffea Spp.", *Cryo–Letters*, vol. 13, No. 5, 297–302 (1992).
Hatanaka et al., "Direct Regrowth of Encapsulated Somatic Embryos of Coffee (Coffea Canephora) After Cooling in Liquid Nitrogen", *Cryo–Letters*, vol. 15, No. 1, 47–52 (1994).
Lecouteux et al., "Cryopreservation of Carrot Somatic Embryos Using a Simplified Freezing Process", *Cryo–Letters*, vol. 12, No. 6, 319–328 (1991).
Tessereau et al., "Cryopreservation of Somatic Embryos: A Tool for Germplasm Storage and Commercial Delivery of Selected Plants", *Annals of Botany*, vol. 74, No. 5, 547–555 (1994).

* cited by examiner

*Primary Examiner*—Vera Afremova
(74) *Attorney, Agent, or Firm*—Winston & Strawn LLP

(57) ABSTRACT

An improved process for the cryo-preservation of plants, especially for the direct cryo-preservation of plant tissues. This process includes the steps of dehydrating, pre-freezing and cryo-freezing plant derived tissue, with the improvement being that the plant tissue to be cryo-preserved is a primary explant that has been subjected an induction treatment for regeneration.

11 Claims, No Drawings

PROCESS FOR THE CRYO-PRESERVATION OF PLANTS

CROSS-REFERENCE TO RELATED APPLICATIONS

This application is a continuation of international application PCT/EP99/07168 filed Sep. 27, 1999, the content of which is expressly incorporated herein by reference thereto.

BACKGROUND OF THE INVENTION

The present invention relates to a process for the direct cryo-preservation of plant tissues wherein the tissues are primary explants that have been subjected to an induction treatment for regeneration.

It is widely acknowledged that for long-term storage of genetic plant material, such as of germplasm of vegetatively propagated species and of recalcitrant species, cryo-preservation is the desired option. This process involves storage at ultra-low temperatures, usually that of liquid nitrogen (−196° C.), at which temperature cell division and metabolic processes come to a stop and the plant material can thus be stored without modification or alteration for prolonged periods of time. Other advantages of this technique reside in that cryo-preserved material requires only limited space, is protected from contamination and needs only moderate maintenance efforts.

Processes for the long-term preservation of plants have been developed only for a restricted number of plant species, wherein the original plant or parts thereof are treated in a number of steps so as to obtain explants in developmental late stages including zygotic and somatic embryos, meristems, etc., which are found to be eventually capable to grow to a new plant after cryo-preservation. However, it is acknowledged that the longer the duration of the in vitro culture before cryo-preservation, that is the higher the number of pretreatment steps, the higher the risk of somaclonal variation and the bigger the amount of laboratory work to prepare the samples to be preserved by freezing. In consequence, said processes may not be applied to a large collection of plant genetic material.

It would therefore be desirable to limit the steps in culture before cryo-preservation to as few as possible.

Apart from the drawbacks involved in subjecting the plant derived tissue to a number of pretreatment steps to arrive at the desired explant tissue that is finally capable to regenerate to a new plant, some developmental stages of the plant, such as, e.g., zygotic embryos, are found to be merely usable for pure lines of self-pollinated species thus limiting the applicability of such procedures. For other species merely vegetative tissues may be used, such as meristems, shoot tips, regenerating tissues or somatic embryos. Consequently, the choice of the specific material for storage will depend on a variety of parameters, such as the plant species, the techniques available, the genetic structure of the plant being stored and the available germplasm.

Finally, in order to limit the risk of somaclonal variation, the preserved tissue should regenerate from the cryo-preserved material as directly as possible into plantlets. Therefore, calli and/or embryogenic tissues are less desirable than somatic embryos, which could directly regrow without any secondary embryogenesis or callogenesis.

SUMMARY OF THE INVENTION

The present invention provides a method for cryogenically storing any one of a wide variety of different plant species without involving the laborious steps of culturing plant material until a later developmental stage of the plant is obtained, ie., one that is capable to grow to a full plant. Thus, different plants may be processed for storage at low temperatures without involving complicated steps to obtain a plant tissue suitable for regeneration to a new plant. This process advantageously includes the steps of dehydrating, pre-freezing and cryo-freezing plant derived tissue, wherein the plant tissue to be cryo-preserved is a primary explant that has been subjected to an induction treatment for regeneration.

In a preferred embodiment, the plant tissue utilized in the process according to the present invention is a primary explant capable to regenerate buds. In another preferred embodiment the process for the cryo-preservation of the present invention comprises using a plant tissue capable to regenerate embryos.

DETAILED DESCRIPTION OF THE PREFERRED EMBODIMENTS

It has been found that the process of the present invention may be applied to any plant/plant material known in the art. It will, however, be mainly applied to plant species, which cannot be stored in an easy way, such as, e.g., semi-recalcitrant plant species or recalcitrant plant species. In another preferred embodiment the plant from which the tissues to be processed for cryo-preservation may be derived, is a plant of the species Theobroma cacao L., that is cacao, or of the species Coffea Canephora or Coffea arabica L., i.e., coffee, or of the species Daucus carota, e.g., carrots.

The induction of the plant tissues may be achieved by cultivating the plant or a particular part thereof, such as, e.g., part of a leaf, part of a stem, a flower bud or hypocotyl segments that have been cut off the plant.

This plant derived tissue may then be transferred to an induction medium, such as, e.g., those described in Driver & Kuniyuki, Hortscience 19 (1984), 507–509; Yasuda, Fuji and Yamaguchi, Plant Cell Physiol. 26 (1985), 595–597; Murashige T. and Skoog F., Physiol. Plant. 15 (1962), 473–497, Berthouly M. and Michaux-Ferriere N., Plant Cell Tiss. Org. Cult. 44 (1996), 169–176 and Halperin, W. 146 (1964), 408–410, which documents are incorporated herein by way of reference. The media may be supplemented by plant hormones such as cytokinines, e.g., 6-benzylaminopurine or kinetin, or auxins, such as 2,4-dichlorophenoxy acetic acid, or mixtures thereof. The skilled artisan will choose the appropriate plant stimulation agent according to his own technical skill. The tissue is then cultivated for a period of time until a primary regenerating tissue is to be observed on the plant derived tissue namely "primary explant".

The present invention is based on the findings that it seemingly is sufficient to merely cultivate a plant derived tissue in an induction medium up to the formation of a primary regenerating tissue and the plant will nevertheless be capable of regenerating into a whole plant after being stored at cryo-preservation conditions.

The period of time for cultivating the plant derived tissue may depend on various parameters, such as the nature of the induction medium utilized and the plant itself, to which the medium is applied, but may be within a period of about 6 months, preferably about 2 months. Based on his own technical knowledge the person skilled in the art will choose the appropriate time period for having the explant forming a primary regenerating tissue.

A preferred induction medium and a preferred expression medium for cacao is the media termed A- and B-, respectively, which contain:

A-medium (Induction for cocoa)

| | |
|---|---|
| $NH_4NO_3$ | 1416 |
| $K_2SO_4$ | 1559 |
| $MgSO_4, 7 H_2O$ | 740 |
| $KH_2PO_4$ | 265 |
| $Ca(NO_3)_2, 2 H_2O$ | 1968 |
| $CaCl_2, 2 H_2O$ | 149 |
| Micro-Nutrients | |
| $Zn(NO_3)_2, 6 H_2O$ | 17.00 |
| $MnSO_4, 1 H_2O$ | 33.50 |
| $CuSO_4, 5 H_2O$ | 0.25 |
| $H_3BO_3$ | 4.80 |
| $Na_2MoO_4, 2 H_2O$ | 0.39 |
| $NiSO_4, 6 H_2O$ | 0.005 |
| $Na_2EDTA$ | 37.3 |
| $FeSO_4, 7 H_2O$ | 27.8 |
| Vitamins | |
| Myo-Inositol | 100 |
| Nicotinic acid | 1 |
| Thiamine HCl($B_1$) | 2 |
| Amino acids | |
| Leucine | 0.4 |
| Arginine | 0.4 |
| Lysine | 0.4 |
| Glycine | 2.0 |
| Tryptophane | 0.2 |
| Plant Hormones | |
| 2,4 dichlorophenoxyacetic acid | 1.0 |
| Kinetin | 0.25 |
| Sucrose | 40 000 |
| Gelrite | 3000 |
| pH 5.5 | |

B-medium (Expression for cocoa)

| | mg/liter |
|---|---|
| Macro-Nutrients | |
| $NH_4NO_3$ | 1416 |
| $K_2SO_4$ | 1559 |
| $MgSO_4, 7 H_2O$ | 740 |
| $KH_2PO_4$ | 265 |
| $Ca(NO_3)_2, 2 H_2O$ | 1968 |
| $CaCl_2, 2 H_2O$ | 149 |
| Micro-Nutrients | |
| $Zn(NO_3)_2, 6 H_2O$ | 17.00 |
| $MnSO_4, 1 H_2O$ | 33.50 |
| $CuSO_4, 5 H_2O$ | 0.25 |
| $H_3BO_3$ | 4.80 |
| $Na_2MoO_4, 2 H_2O$ | 0.39 |
| $NiSO_4, 6 H_2O$ | 0.005 |
| $Na_2EDTA$ | 37.3 |
| $FeSO_4, 7 H_2O$ | 27.8 |
| Vitamins | |
| Myo-Inositol | 100 |
| Nicotinic acid | 1 |
| Thiamine HCl($B_1$) | 2 |
| Amino acids | |
| Leucine | 0.4 |
| Arginine | 0.4 |
| Lysine | 0.4 |
| Glycine | 2.0 |
| Tryptophane | 0.2 |
| Sucrose | 40 000 |
| Gelrite | 3000 |
| pH 5.5 | |

Another preferred induction medium and expression medium for cacao, termed medium C and medium D, respectively, are mainly used for cocoa and contain:

C-medium (Induction for cocoa)

| | mg/liter |
|---|---|
| Macro-Nutrients (Murashige and Skoog, 1962) | |
| $NH_4NO_3$ | 1650.00 |
| $KNO_3$ | 1900.00 |
| $MgSO_4, 7 H_2O$ | 370.0 |
| $KH_2PO_4$ | 170.0 |
| $CaCl_2, 2 H_2O$ | 440.0 |
| Micro-Nutrients (Murashige and Skoog, 1962) | |
| $ZnSO_4, 7 H_2O$ | 10.600 |
| $MnSO_4, 1 H_2O$ | 16.900 |
| $CuSO_4, 5 H_2O$ | 0.025 |
| $H_3BO_3$ | 6.200 |
| $Na_2MaO_4, 2 H_2O$ | 0.250 |
| $CoCl_2, 6 H_2O$ | 0.025 |
| KI | 0.830 |
| $Na_2EDTA$ | 37.3 |
| $FeSO_4, 7 H_2O$ | 27.8 |
| Vitamins (from B5 Gamborg medium) | |
| Meso - Inositol | 100.0 |
| Pyridoxine HCl ($B_6$) | 0.7 |
| Nicotinic acid | 0.5 |
| Thiamine HCl ($B_1$) | 0.7 |
| Adenine sulfate | 0.5 |
| Glycine | 2.0 |
| L Lysine | 0.4 |
| L Leucine | 0.4 |
| L Arginin | 0.4 |
| L Tryptophane | 0.2 |
| Plant Hormones | |
| AIA | 0.05 |
| AIB | 0.05 |
| $GA_3$ | 0.02 |
| Sucrose | 20 000 |
| Maltose | 20 000 |
| Gelrite | 3.000 |
| pH | 5.6 |

T. Murashige and F. Skoog, Physiol. Plant. 15, 473–497 (1962)

D-medium (Expression for cocoa)

| | mg/liter |
|---|---|
| Macro-Nutrients (Murashige and Skoog, 1962) | |
| $NH_4NO_3$ | 1650.00 |
| $KNO_3$ | 1900.00 |
| $MgSO_4, 7 H_2O$ | 370.0 |

-continued

D-medium (Expression for cocoa)

| | mg/liter |
|---|---|
| $KH_2PO_4$ | 170.0 |
| $CaCl_2$, 2 $H_2O$ | 440.0 |
| Micro-Nutrients (Murashige and Skoog, 1962) | |
| $ZnSO_4$, 7 $H_2O$ | 10.600 |
| $MnSO_4$, 1 $H_2O$ | 16.900 |
| $CuSO_4$, 5 $H_2O$ | 0.025 |
| $H_3BO_3$ | 6.200 |
| $Na_2MoO_4$, 2 $H_2O$ | 0.250 |
| $CoCl_2$, 6 $H_2O$ | 0.025 |
| KI | 0.830 |
| $Na_2$EDTA | 37.3 |
| $FeSO_4$, 7 $H_2O$ | 27.8 |
| Vitamins (from B5 Gamborg medium) | |
| Meso - Inositol | 100.0 |
| Pyridoxine HCl ($B_6$) | 0.7 |
| Nicotinic acid | 0.5 |
| Thiamine HCl ($B_1$) | 0.7 |
| Adenine sulfate | 0.5 |
| Glycine | 2.0 |
| L Lysine | 0.4 |
| L Leucine | 0.4 |
| L Arginin | 0.4 |
| L Tryptophane | 0.2 |
| Sucrose | 40 000 |
| Gelrite | 3.000 |
| Coco milk | 100 ml |
| pH | 5.6 |

T. Murashige and F. Skoog, Physiol. Plant. 15, 473–497 (1962)

This primary regenerating tissue may then be treated by dehydration, prefreezing and cryo-freezing.

In order to perform the dehydration step any means known in the art to dehydrate the priar explant to an extent that no intracellular ice crystallization occurs upon the subsequent freezing steps may be envisaged. Such means include, e.g., placing explants or pretreated explants or pretreated and encapsulated explants n the air current of a lamninar flow cabinet, in a stream of compressed air, in an airtight container together with silica gel or in an airtight container together with various oversaturated salt solutions, that control the relative humidity of the atmosphere.

In a preferred embodiment it has been shown that a two step protocol involving the use of a 0.4 M sucrose solution in the first step and a 1.0 M sucrose solution in the second step works quite acceptable. The time period required for carrying out steps 1 and 2 vary with respect to the plant to be treated but may well be within a time period of about 10 days, preferably about 4 days.

The pre-freezing step may also be carried out according to techniques well known in the art, such as, e.g., at temperatures of from about −10 to about −40° C., most preferably at a temperature of about −25° C. To this end the cryotubes containing the plant derived tissue to be preserved are preferably placed in a vessel containing an appropriate freezing medium, such as ethanol or isopropanol, at room temperature and the vessel is then transferred into a freezer to slowly cool the sample to the above mentioned temperature. Usually the time period for pre-freezing the sample varies of from 10 to 30 hrs, preferably 15 hrs or more, most preferred about 20 hrs.

Subsequently to the pre-freezing step the tube or vessel containing the induced primary explant may directly be transferred into liquid nitrogen for long term storage.

The primary explants treated accordingly are found to be capable to regenerate to a full plant after the cryo-preservation.

EXAMPLES

The invention will now be explained according to the following limiting examples, which are for illustrative purposes only and shall not be construed to limit the invention as defined by the appended claims.

Example 1

Cocoa (Genotype a: an Eucadorian Hybrid Genotype Termed EET 95)

In this example a process for the in vitro conservation of cocoa genetic resources using cryo-preservation of pieces of flower bud is described.

From cocoa trees growing and flowering in fields or in greenhouses young and immature flower buds were collected. Immediately after collection they were sterilized and opened in order to place them onto an induction medium, termned A-medium (supra). After 3 weeks of culture, they were subcultured on a second medium, called B-medium (supra) for two 3-week culture cycles. Primary embryogenic calli appear during this last culture phase observed by determining the first globular stages among the cells of the primary calli. In the case of creating an embryogenic strain, these calli will be placed on a multiplication medium in order to establish and to maintain a stable proliferation of embryogenic cells.

In this example the cryo-preservation ability of induced explants after 6 weeks of culture (3 weeks on A-medium and 3 weeks on B-medium) was investigated. Therefore, freezing experiments were preformed using explants taken before their second transfer onto B-medium.

The freezing protocol used included two phases. The first one is a two-step sucrose pretreatment. The second one is a two-step cooling phase including a first step in a standard freezer (−25° C.) before direct immersion in liquid nitrogen. The explants were pretreated first in a 0.4 M sucrose solution for a 3-day period. Then they were transferred to a 1.0 M sucrose solution for a 1-day period before freezing. Pretreated explants are divided into 4 to 6 parts and are then placed into cryotubes (Corning, disposable sterile cryogenic vials, 2 ml, Cat. No. 25704) in a 1.0 M sucrose solution. The cryotubes are placed in a vessel containing isopropanol, which vessel is transferred to a standard freezer for 20 h. Subsequently, the cryotubes were immersed in liquid nitrogen and stored for 6 months.

For recovery the samples were rapidly thawed by agitation for 2–3 mnin in a water bath at +40° C.

The samples were then placed on medium A supplemented with 0.8 M sucrose and are then progressively rebydrated by daily subculture on the same medium containing a decreasing sucrose concentration (0.2 M sucrose/day) until the sugar concentration reached that of the standard medium (medium A). After about 1 week the samples are transferred to medium B.

The results of the table 1 show that the pre-freezing temperature may influence the success of the cryo-preservation of induced primary explants. Using both staminodes and etamines as floral piece, the ability to regenerate to plants after freezing in liquid nitrogen was shown.

As a control, plant tissues without any cryo-preservation treatment have been used. The regeneration procedure followed that currently used with non cryo-preserved tissue as it has been described by Lopez O., Bollon H., Eskes A., and Petiard V., C.R.Acad.Sci. Paris 316 (1993), 579–584 or modified from Li Z., Traore A., Maximova S. and Guiltinan M. J., In Vitro Cell.Dev.Biol. 34 (1998), 1–8.

TABLE 1

Effect of the pre-freezing temperature on the regeneration ability of induced primary explants formed from staminodes and etamines after cryo-preservation in liquid nitrogen

| Pre-freezing temperature | Number of pieces | Number of explants | After freezing in LN[1]<br>Rate of regenerating explants (%) |
|---|---|---|---|
| Control | 60 | 60 | None |
| −20° C. | 20 | 110 | 18 |
| −25° C. | 20 | 116 | 44 |
| −40° C. | 20 | 129 | 12 |

[1]LN = liquid nitrogen

Example 2

Cacao (Genotype b: Brasilian Genotype Termed MAN 15-2)

In the following example the same freezing protocol as in example 1 has been used with the proviso of a change in the pretreatment phase and the cocoa genotype. The plant derived tissues were explants derived from 6-week old staminodes cultures.

The effect of the duration of pretreatment and in particular the incubation period in 0.4 M and 1.0 M sucrose solution associated to a pre-freezing temperature of −25° C. has been studied.

TABLE 2

Cryo-preservation of primary explant according to the pretreatment duration

| Pretreatment duration (days) (0.4 M/1.0 M sucrose) | Number of explants | After freezing in LN[1]<br>Rate of regenerating explants (%) |
|---|---|---|
| Control | 60 | None |
| 4d (3d/1d) | 39 | 39 |
| 7d (6d/1d) | 42 | 51 |
| 10d (7d/3d) | 38 | 31 |

[1]LN = liquid nitrogen

From the above it may be derived that the regeneration ability may be improved by subjecting the primary explants to a short pretreatment associated with a 1-day incubation in 1.0 M sucrose solution.

Example 3

In this example the effect of the culture duration of the primary explant before cryo-preservation has been studied. Unless otherwise indicated all steps are as detailed in example 1. The freezing protocol with explants (staminodes) directly placed on pretreatment medium after collection or placed on pretreatment medium after only one week of culture on A-medium has been applied.

TABLE 3

Cryo-preservation of primary explants according to culture duration in A-medium

| Culture conditions of explants | Number of pieces | Number of explants | Rate of regenerating explants (%) after freezing in LN[1] |
|---|---|---|---|
| Control | 10 | 40 | None |
| Without culture on A medium | 10 | 40 | 20 |
| 1 week of culture on A-medium | 8 | 32 | 62 |

[1]LN = liquid nitrogen

The results summarized in the above table show that cryo-preserved explants are able to regenerate after freezing without or with a very short culture period in the induction medium (A-medium). However, it appears that it is better to cultivate explants on induction medium before cryo-preservation to obtain a high frequency of regenerating explants.

Example 4

In this example a process for freezing primary explants using the pretreatment—dehydration technique is illustrated. Pretreatment is based on a stepped increase of the sucrose content in the culture medium (0.25 M/3d; 0.5 M/5d; 0.75 M/5d; 1.0 M/2d). Then pretreated explants were dehydrated under 43% relative humidity at 24° C. in a desiccator. After various dehydration steps the samples are directly immersed in liquid nitrogen.

TABLE 4

Cryo-preservation of primary explants according to the pretreatment-dehydration protocol

| Conditions | Water content (g/100 g dwt) | Number of explants | After freezing in LN[1]<br>Rate of regenerating explants (%) |
|---|---|---|---|
| Control | | 110 | None |
| Pretreated | 185 | 12 | 90 |
| Dried 38 hrs | 52 | 42 | 20 |
| Dried 48 hrs | 40 | 20 | 30 |
| Dried 62 hrs | 28 | 16 | 5 |

[1]LN = liquid nitrogen

The results of the above table show that another technical approach compared to the desiccation method can be developed and optimized for pretreating primary explants before freezing in liquid nitrogen without essentially altering their ability to regenerate into plants.

Example 5

(a) *Coffea Canephora Robusta* (of Vanuatu Origin, Labeled J21)

Leaf explants are harvested on trees growing in fields or in nurseries or in greenhouses, then sterilized and placed in culture under aseptic conditions onto an induction medium.

A preferred induction medium for *Coffea canephora* is the medium termed E which contains:

| E medium (Induction for *Coffea canephora*) | |
|---|---|
| | mg/liter |
| Macro-Nutrients (Yasuda, supra) | |
| $NH_4NO_3$ | 412 |
| $KNO_3$ | 475 |
| $MgSO_4$, 7 $H_2O$ | 92.5 |
| $KH_2PO_4$ | 85 |
| $CaCl_2$, 2 $H_2O$ | 110 |
| Micro-Nutrients (Yasuda, supra) | |
| $ZnSO_4$, 7 $H_2O$ | 4.30 |
| $MnSO_4$, 1 $H_2O$ | 6.80 |
| $CuSO_4$, 5 $H_2O$ | 0.05 |
| $H_3BO_3$ | 3.80 |
| $Na_2MoO_4$, 2 $H_2O$ | 0.125 |
| $Na_2EDTA$ | 37.3 |
| $FeSO_4$, 7 $H_2O$ | 27.8 |

-continued

E medium (Induction for *Coffea canephora*)

|  | mg/liter |  |
|---|---|---|
| Vitamins (from B5 Gamborg medium) |  |  |
| Meso-Inositol | 100.0 |  |
| Pyridoxine HCl ($B_6$) | 1.0 |  |
| Nicotinic acid | 1.0 |  |
| Thiamine HCl($B_1$) | 10 |  |
| Plant hormone |  |  |
| BAP (6 benzylaminopurine) | 1 |  |
| Sucrose | 30 | 000 |
| Bacto-Difco agar | 8 | 000 |
| pH 5.6 |  |  |

Vitamins $B_5$: Gamborg et al., In vitro, 12 (1976), 473–478.

Primary embryogenic calli appear on the leaf explant during a culture period of 1 to 6 months depending on the genotype and the number of intermediate subcultures.

The freezing protocol used in this example was as described in example 1, above. Leaf explants are pretreated with high sucrose concentration of 1.0 M and are then frozen in liquid nitrogen using the above-described 2-step cooling method.

The effect of the culture time on the induction medium on the appearance of proliferating calli for both control and cryo-preserved explants has been studied. No subculture has been performed. Table 5 shows that starting from 2 to 6 months the rate of primary calli formation on leaf explants is approximately the same. After cryo-preservation roughly the same rate of reproliferating calli is observed.

TABLE 5

Cryo-preservation of induced leaf explant of *Coffea canephora*

| Culture duration of the leaf explant before freezing | Control Rate of primary calli | Viability after storage in liquid nitrogen Rate of primary calli |
|---|---|---|
| 2 months | 95 | 43 |
| 4 months | 95 | 65 |
| 6 months | 91 | 48 |

(b) *Coffea Arabica* Variety Typical

Leaf explants are harvested on a tree (or on a microcutting) then sterilized and placed in culture under aseptic conditions on to induction medium. The inductive medium below, termed F-medium, is used as preferred induction medium for *Coffea arabica* L.

F-medium (expression for *Coffea arabiea*)

|  | mg/liter |
|---|---|
| Macro-Nutrients (MS)/2 (Murashige and Skoog, 1962) |  |
| $NH_4NO_3$ | 1650.00 |
| $KNO_3$ | 1900.00 |
| $MgSO_4$, 7 $H_2O$ | 370.0 |
| $KH_2PO_4$ | 170.0 |
| $CaCl_2$, 2 $H_2O$ | 440.0 |

-continued

F-medium (expression for *Coffea arabiea*)

|  | mg/liter |  |
|---|---|---|
| Micro-Nutrients (MS)/2 Micro-Nutrients (Murashige and Skoog, 1962) |  |  |
| $ZnSO_4$, 7 $H_2O$ | 10.600 |  |
| $MnSO_4$, 1 $H_2O$ | 16.900 |  |
| $CuSO_4$, 5 $H_2O$ | 0.025 |  |
| $H_3BO_3$ | 6.200 |  |
| $Na_2MoO_4$, 2 $H_2O$ | 0.250 |  |
| $CoCl_2$, 6 $H_2O$ | 0.025 |  |
| KI | 0.830 |  |
| $Na_2$EDTA | 37.3 |  |
| $FeSO_4$, 7 $H_2O$ | 27.8 |  |
| Vitamins (from B5 Gamborg medium) |  |  |
| Meso-Inositol | 100.0 |  |
| Pyridoxine HCl ($B_6$) | 1.0 |  |
| Nicotinic acid | 1.0 |  |
| Thiamine HCl ($B_1$) | 10 |  |
| Glycine | 1.0 |  |
| Casein hydrolysate | 100 mg |  |
| Malt extract broth | 400 mg |  |
| Plant hormones |  |  |
| AIB | 1.0 |  |
| 2,4-D | 0.5 |  |
| 2IP | 2.0 |  |
| Sucrose | 30 | 000 |
| Gelrite | 2.5000 |  |
| pH | 5.6 |  |

T. Murashige and F. Skoog, Physiol. Plant. 15, 473–497 (1962)

In the case of *Coffea arabica*, the expression of embryogenic capacities is made after transfer of induced primary explants on a second medium termed medium G, after about one month of culture on the F-medium and which contains:

G-medium (expression for *Coffea arabica*)

|  | mg/liter |
|---|---|
| Macro-Nutrients (MS)/2 (Murashige and Skoog, 1962) |  |
| $NH_4NO_3$ | 1650.00 |
| $KNO_3$ | 1900.00 |
| $MgSO_4$, 7 $H_2O$ | 370.0 |
| $KH_2PO_4$ | 170.0 |
| $CaCl_2$, 2 $H_2O$ | 440.0 |
| Micro-Nutrients (Murashige and Skoog, 1962) |  |
| $ZnSO_4$, 7 $H_2O$ | 10.600 |
| $MnSO_4$, 1 $H_2O$ | 16.900 |
| $CUSO_4$, 5 $H_2O$ | 0.025 |
| $H_3BO_3$ | 6.200 |
| $Na_2MoO_4$, 2 $H_2O$ | 0.250 |
| $CoCl_2$, 6 $H_2O$ | 0.025 |
| KI | 0.830 |
| $Na_2$EDTA | 37.3 |
| $FeSO_4$, 7 $H_2O$ | 27.8 |
| Vitamins |  |
| Myo-Inositol | 200.0 |
| Adenin Sulfate | 6.0 |
| Cystein | 40.0 |
| Thiamine HCl ($B_1$) | 20 |
| Glycine | 20.0 |
| Casein hydrolysate | 200 mg |
| Malt extract broth | 809 mg |
| 2,4-D | 1.0 |
| BAP | 4.0 |

-continued

| G-medium (expression for *Coffea arabica*) | |
|---|---|
| | mg/liter |
| Sucrose | 30 000 |
| Gelrite | 2.5000 |
| pH | 5.6 |

T. Murashige and F. Skoog, Physiol. Plant. 15, 473–497 (1962)

Primary calli appeared on the leaf explant during a culture period of 1 to 4 months depending on the genotype and the number of intermediate subcultures.

The freezing protocol used in this example was as described in example 1, above. Leaf explants were pretreated with high sucrose concentrations in two successive steps: 6 days in induction medium (F-medium) supplemented with 0.4 M sucrose then a second step of 1 day in the F-medium supplemented with 1.0 M sucrose. Then, the samples are frozen in liquid nitrogen using the above-described 2-step cooling method.

The effects of culture time on the induction medium and of prefreezing temperature on the appearance of proliferating calli for both control and cryo-preserved explants has been studied. Subcultures have been performed each month. Table (5 bis) shows that high frequencies of regenerating calli were obtained for explants cultured during one month on inductive medium and pre-frozen at −25° C. before immersion in liquid nitrogen. The increase of culture duration on induction medium leads to a decrease on the viability after freezing for *C. arabica*.

| | Viability after storage in liquid nitrogen Prefreezing temperatures | | | |
|---|---|---|---|---|
| | −25° C. | | −35° C. | |
| Culture period (d) | Rate of regrowing calli (%) | Rate of regenerating calli (%) | Rate of regrowing calli (%) | Rate of regenerating calli (%) |
| 0 | 0 | 0 | | |
| 14 | 63 | 45 | 0 | 0 |
| 30 | 90 | 90 | 14.3 | 9.3 |
| 90 | 0 | 0 | 0 | 0 |

Note:
For control, 96% of explant produce calli and 28% are able to regenerate plants by somatic embryogenesis.

Example 6

Two other *Coffea canephora* genotypes (of Vanuatu origin, labeled NC 8 and NC 109, respectively) have been investigated. Table 6 shows a high level of regrowth after cryo-preservation and the effective production of plantlets obtained from primary embryos selected on the new embryogenic proliferation after freezing. These plantlets were finally developed into whole trees which behave as non cryo-preserved ones.

TABLE 6

Regeneration of plantlets from cryo-preserved leaf explants of *Coffea canephora*

| | Cryo-preserved explants | | Conversion rate (%) into plantlets of primary embryos formed from cryo-preserved explants | |
|---|---|---|---|---|
| Geno-types | Rate (%) of regrowing calli | Rate (%) of embryogenic calli | Pretreated | Cryo-preserved |
| NC8 | 84 | 50 | 30 | 22 |
| 109 | 100 | 75 | 30 | 25 |

Example 7 (Carrot)

In the case of carrot somatic embryogenesis, most of the embryogenic strains are initiated from hypocotyl segments of a germinating seed. These pieces of hypocotyl have been obtained by cultivation on the following induction medium termed H:

H-medium used as preferred induction medium for carrot (*Daucus carota L.*):

| | mg/liter | |
|---|---|---|
| Macro-Nutrients | | |
| $NH_4NO_3$ | 1650.00 | |
| $KNO_3$ | 1900.00 | |
| $MgSO_4$, 7 $H_2O$ | 370.0 | |
| $KH_2PO_4$ | 170.0 | |
| $CaCl_2$, 2 $H_2O$ | 440.0 | |
| Micro-Nutrients (Murashige and Skoog, 1962) | | |
| $ZnSO_4$, 7 $H_2O$ | 10.600 | |
| $MnSO_4$, 1 $H_2O$ | 16.900 | |
| $CuSO_4$, 5 $H_2O$ | 0.025 | |
| $H_3BO_3$ | 6.200 | |
| $Na_2MoO_4$, 2 $H_2O$ | 0.250 | |
| $CoCl_2$, 6 $H_2O$ | 0.025 | |
| KCl | 0.830 | |
| $Na_2EDTA$ | 37.3 | |
| $FeSO_4$, 7 $H_2O$ | 27.8 | |
| Vitamins (Halperin, 1964) | | |
| Adenine | 2.0 | |
| Thiamine HCl ($B_1$) | 5.0 | |
| Nicotinic acid | 5.0 | |
| Thiamine HCl ($B_1$) | 5.0 | |
| 2,4-D | 0.1 | |
| Sucrose | 20 | 000 |
| Bacto-Difco agar | 8 | 000 |
| pH 5.8 | | | for a time period of about 3 to 4 weeks. After observing the formation of primary calli, usually after 3 weeks the explants are treated as described below.

A freezing protocol based on first inducing desiccation tolerance and second dehydrating under controlled relative humidity was applied with finally a direct immersion in liquid nitrogen.

Desiccation tolerance is induced by culture of hypocotyl explants on the above induction medium (H-medium) supplemented with 0.4 M–0.5 M sucrose concentration.

Dehydration is performed by equilibration of the tissues under controlled relative humidity in the range of 43% to 11% at 24° C. during 7 days. Subsequently the dried explants are directly immersed in liquid nitrogen.

TABLE 7

Cryo-preservation of carrot hypocotyl using a desiccation method

| Starting conditions | Number of explants | After drying under 43% and freezing in LN | |
|---|---|---|---|
| | | Rates of surviving explants (%) | Rates of embryogenic explants (%) |
| Without culture on induction medium | 30 | 23 | 13 |
| After 3 week culture on induction medium | 30 | 66 | 33 |

It is shown that the initial culture phase on the induction medium before freezing improves the success of the cryo-preservation of carrot primary explant.

From the above examples it could be clearly seen that cryo-preservation of primary explants capable to regenerate plants was successfully performed with cocoa, coffee and carrot species, a recalcitrant, semi-recalcitrant and orthodox species respectively. The primary explants used are pieces of flower bud, pieces of leaves and hypocotyl segments, respectively, according to the organ already known as capable to regenerate. Induction of freezing tolerance using a hardening-off treatment in presence of high sucrose concentrations has exemplarily been used. Various freezing methods can be used, i.e., the already described method with some simplifications as a pre-freezing step at preferably about −25° C. or a partial dehydration before freezing for species known to be desiccation sensitive (cacao, coffee) and a desiccation before freezing for carrot which is considered as desiccation tolerant species.

According to the present invention the time period to introduce an accession in a cryo-preserved gene bank could enormously be reduced while preserving the capability to regenerate into a plants after cryo-preservation. The process described allows to envisage long-term storage of genetic resources for large collection of different species and specially the tropical ones without the drawbacks inherent to the establishment and maintenance of in vitro culture.

What is claimed is:

1. A process for the cryo-preservation of a primary regeneration tissue derived from cocoa plant or a coffee plant comprising the following steps:
    cultivating a plant tissue derived from cocoa plant or a coffee plant on an induction medium for a time sufficient to induce a primary regeneration tissue comprising embryogenic cells;
    culturing the primary regenerating tissue on a multiplication medium for a time sufficient to maintain a stable proliferation of the primary regeneration tissue;
    treating the primary regeneration tissue in a two step process that comprises sequential incubation in first and second sucrose media, wherein the second medium contains a greater amount of sucrose than the first medium;
    prefreezing the primary regenerating tissue to a temperature between −20° C. and −40° C.; and
    cryofreezing the primary regeneration tissue.

2. The process of claim 1, wherein the treating step further comprises a dehydration step and wherein the dehydration step involves placing the primary regeneration tissue in an air current of a laminar flow cabinet, in a stream of compressed air, or in an airtight container together with silica gel or various over-saturated salt solutions to control the relative humidity.

3. The process of claim 1, wherein the plant tissue utilized is derived from *Coffea canephora* or *Coffea arabica*.

4. The process of claim 1, wherein the plant tissue utilized is derived from *Theobroma cacao*.

5. A process for the cryo-preservation of a primary regeneration tissue derived from a cocoa plant or a coffee plant comprising the steps of:
    incubating a plant tissue derived from a cocoa plant or a coffee plant in an induction medium for a time sufficient to induce a primary regeneration tissue comprising embryogenic cells;
    pretreating the primary regeneration tissue by culturing the primary regeneration tissue on successive culture media with an increasing concentration of sucrose; and
    cryofreezing the primary regeneration tissue.

6. The process of claim 5, further comprising the step of culturing the primary regeneration tissue on a multiplication medium for a time sufficient to maintain a stable proliferation of primary regeneration tissue before step of pretreating.

7. The process of claim 5, further comprising the step of prefreezing the primary regeneration tissue to a temperature between −20° C. and −40° C. before step of crupfreezing.

8. The process of claim 5, wherein the step of pretreating the primary regeneration tissue comprises first incubating the primary regeneration tissue in a medium containing 0.4 M sucrose followed by incubating the primary regeneration tissue in a medium containing 1 M sucrose.

9. The process of claim 5, wherein the step of pretreating the primary regeneration tissue comprises culturing the primary regeneration tissue in medium containing 0.25 M sucrose, followed by culturing on a medium containing 0.5 M sucrose, followed by culturing on a medium containing 0.75 M sucrose, which is followed by culturing the primary regeneration tissue on a medium containing 1.0 M sucrose.

10. The process of claim 1, wherein the step of treating comprises first incubating the primary regeneration tissue in a medium containing 0.4 M sucrose followed by the incubation of the primary regeneration tissue in a medium containing 1 M sucrose.

11. The process of claim 1, wherein the temperature of the prefreezing step is minus 25° C.

* * * * *

UNITED STATES PATENT AND TRADEMARK OFFICE
CERTIFICATE OF CORRECTION

PATENT NO. : 6,783,984 B2
DATED : August 31, 2004
INVENTOR(S) : Florin et al.

It is certified that error appears in the above-identified patent and that said Letters Patent is hereby corrected as shown below:

<u>Column 14,</u>
Line 34, after "between –20°C. and –40°C. before step of", delete "crupfreezing" and insert -- cryofreezing --.

Signed and Sealed this

Seventh Day of December, 2004

JON W. DUDAS
*Director of the United States Patent and Trademark Office*